United States Patent [19]
Quedens et al.

[11] Patent Number: 5,205,288
[45] Date of Patent: Apr. 27, 1993

[54] FETAL ELECTRODE PRODUCT WITH FEMALE SOCKET CONNECTOR AND CONNECTOR DEVICE WITH MALE PLUG CONNECTOR EACH FOR USE IN MONITORING FETAL HEART RATE

[75] Inventors: Phillipp J. Quedens, Berlin; Donald R. Boucher, Wallingford; John T. Shipherd, Madison; James W. Poirier, Northford, all of Conn.

[73] Assignee: American Home Products Corporation, New York, N.Y.

[21] Appl. No.: 772,691

[22] Filed: Oct. 7, 1991

Related U.S. Application Data

[63] Continuation-in-part of Ser. No. 661,253, Feb. 26, 1991, Pat. No. 5,168,876, and a continuation-in-part of Ser. No. 605,843, Oct. 30, 1990.

[51] Int. Cl.⁵ .......................................... A61B 5/0444
[52] U.S. Cl. .................................... 128/642; 128/698; 128/785
[58] Field of Search ............................. 128/639–642, 128/783–785, 698; 439/909, 668–669, 825, 842

[56] References Cited

U.S. PATENT DOCUMENTS

| | | | |
|---|---|---|---|
| Re. 28,990 | 10/1976 | Hon et al. | 128/640 |
| Re. 32,204 | 7/1986 | Halvorsen | 128/642 |
| 2,318,207 | 5/1943 | Ellis | 128/407 |
| 3,234,500 | 2/1966 | Buckland | 439/669 |
| 3,580,242 | 5/1971 | La Croix | 128/640 |
| 3,800,800 | 4/1974 | Garbe et al. | 128/408 |
| 3,895,635 | 7/1975 | Justus et al. | 128/640 |
| 4,061,408 | 12/1977 | Bast et al. | 339/75 R |
| 4,073,287 | 2/1978 | Bradley et al. | 128/2 R |
| 4,090,760 | 5/1978 | Furey | 339/61 R |
| 4,094,571 | 6/1978 | Benjamin | 339/91 R |
| 4,121,573 | 10/1978 | Crovella et al. | 128/696 |
| 4,180,080 | 12/1979 | Murphy | 128/642 |
| 4,209,020 | 6/1980 | Nielsen | 128/640 |
| 4,253,721 | 3/1981 | Kaufman | 339/91 R |
| 4,268,101 | 5/1981 | Stone | 339/61 R |
| 4,320,764 | 3/1982 | Hon | 128/635 |
| 4,321,931 | 3/1982 | Hon | 128/642 |
| 4,353,372 | 10/1982 | Ayer | 128/640 |
| 4,384,757 | 5/1983 | Andrews, Jr. et al. | 339/258 R |
| 4,437,467 | 3/1984 | Helfer et al. | 128/642 |
| 4,522,211 | 6/1985 | Bare et al. | 128/640 |
| 4,632,121 | 12/1986 | Johnson et al. | 128/639 |
| 4,671,591 | 6/1987 | Archer | 439/346 |
| 4,848,345 | 7/1989 | Zenkich | 128/419 D |
| 4,894,023 | 1/1990 | Hall | 439/278 |
| 4,911,657 | 3/1990 | Berlin | 439/502 |
| 5,046,965 | 9/1991 | Neese et al. | 439/372 |

FOREIGN PATENT DOCUMENTS

| | | |
|---|---|---|
| 0377432 | 7/1990 | European Pat. Off. |
| 8603542 | 5/1986 | Fed. Rep. of Germany |
| 8701828 | 4/1987 | Fed. Rep. of Germany |
| 1339029 | 11/1973 | United Kingdom |
| 2057784 | 4/1981 | United Kingdom |

OTHER PUBLICATIONS

Corometrics Medical Systems, Inc., Leg Plate For Use With Corometrics Model 115, 116 Fetal Monitors, as offered for sale in Catalog No. 2608DA0, Sep./1988, 5 pages.

Primary Examiner—Lee S. Cohen
Assistant Examiner—Jeffrey R. Jastrab
Attorney, Agent, or Firm—Darby & Darby

[57] ABSTRACT

A female fetal electrode product includes a socket connector electrically connected to fetal and maternal electrodes. The female connector shrouds and electrically connects with a male plug connector. The electrodes may be electrically connected with a remote monitoring device via the male and female connectors. The male connector may extend within an opening in the leg plate or project from the leg plate and may be removable from the leg plate. The female socket connector has an outer dimension less than the inner dimension of a driving tube so that the driving tube can be pulled over the female socket connector after the fetal electrode has been attached to a fetus.

24 Claims, 2 Drawing Sheets

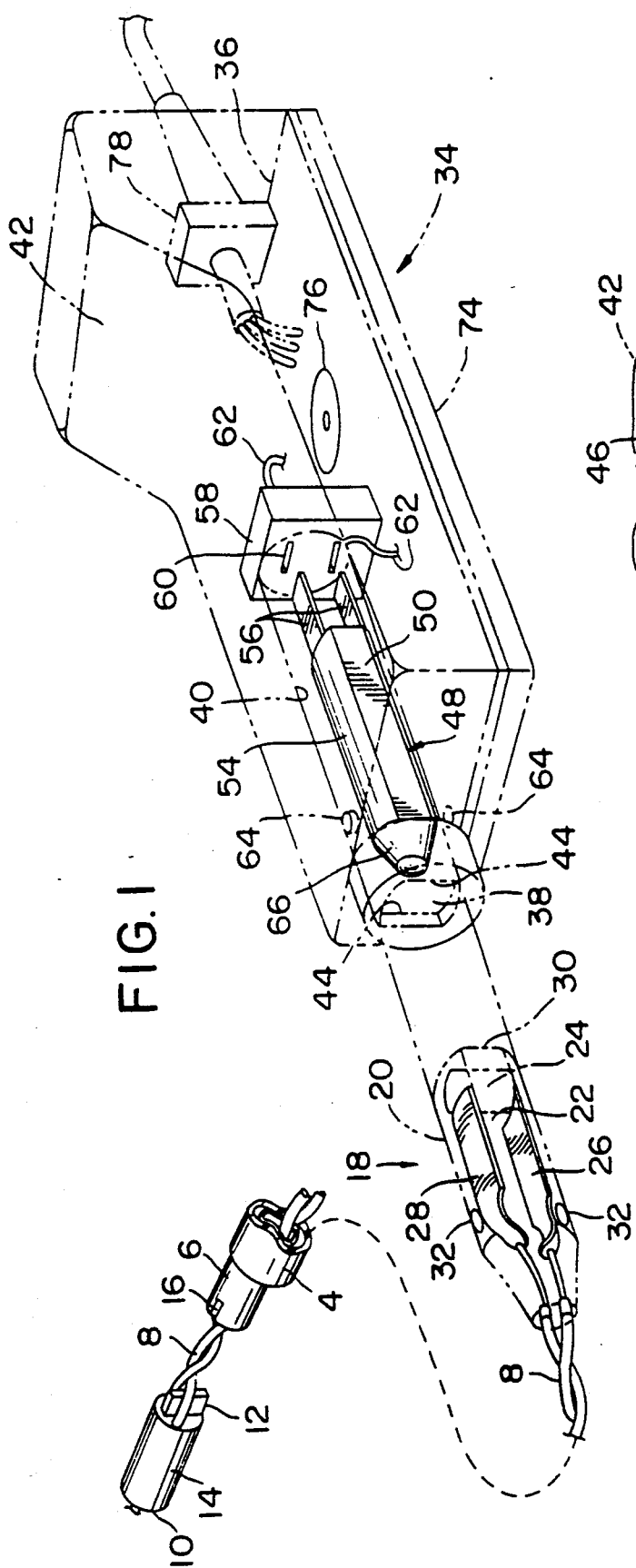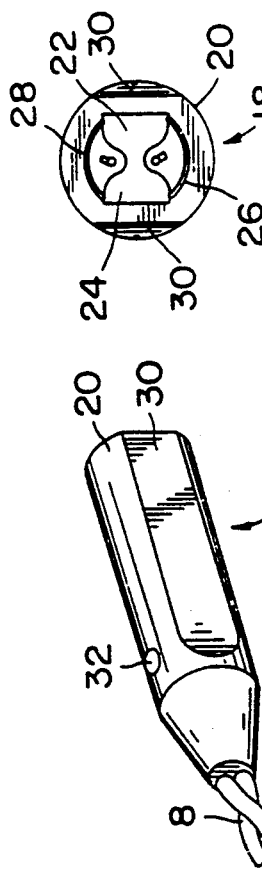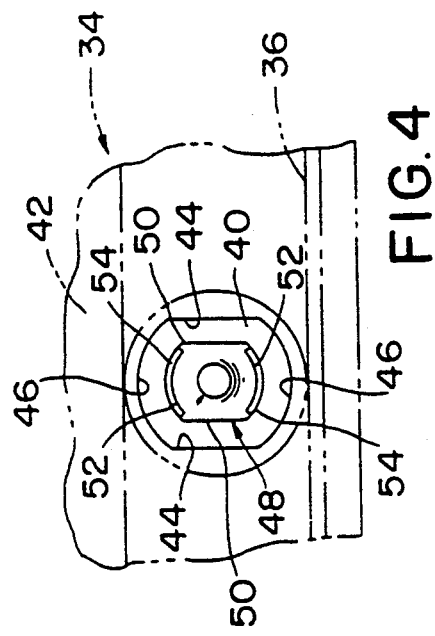

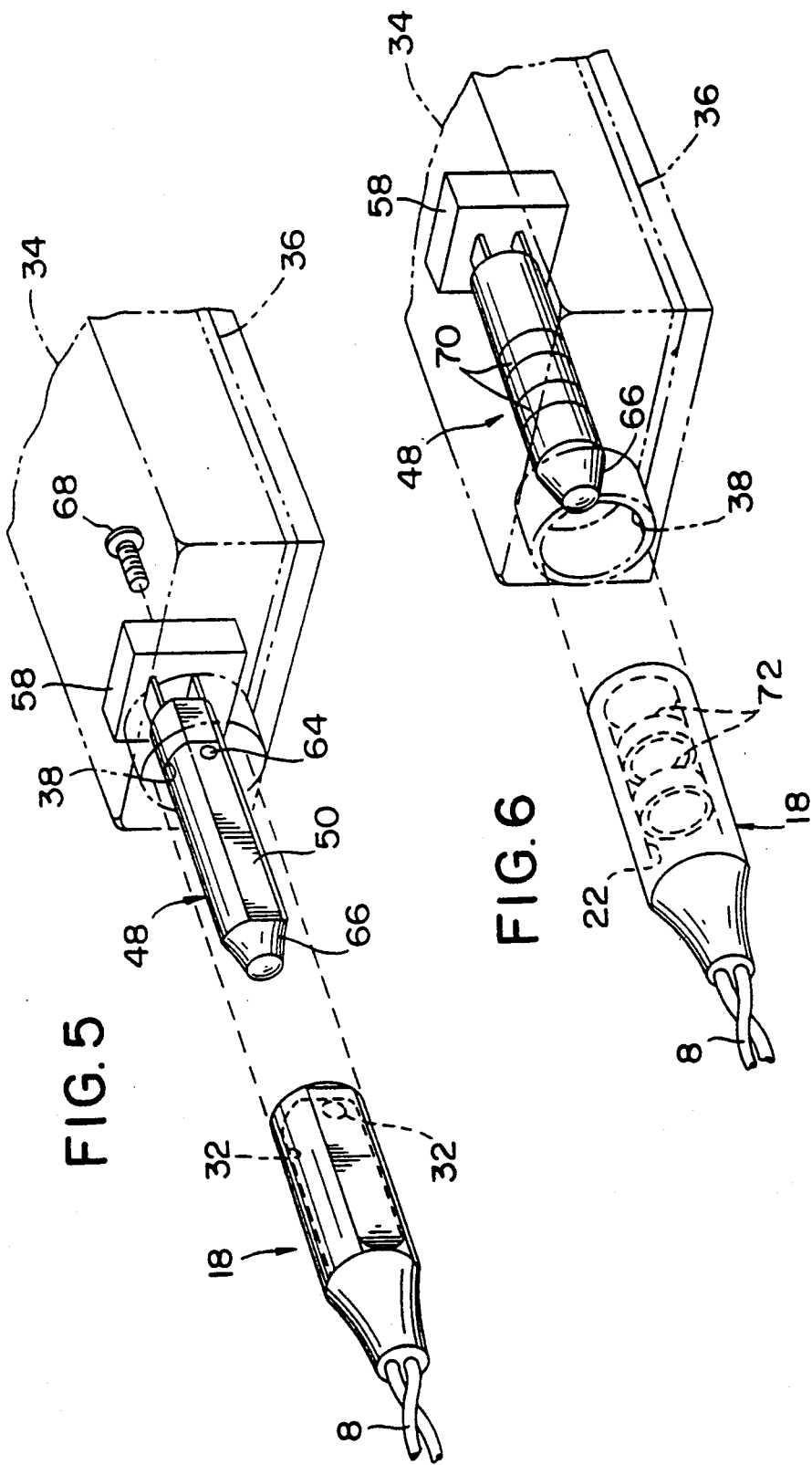

FETAL ELECTRODE PRODUCT WITH FEMALE SOCKET CONNECTOR AND CONNECTOR DEVICE WITH MALE PLUG CONNECTOR EACH FOR USE IN MONITORING FETAL HEART RATE

CROSS-REFERENCE TO COPENDING APPLICATIONS

This is a continuation-in-part of U.S. patent application Ser. No. 07/661,253, filed Feb. 26, 1991, now U.S. Pat. No. 5,168,876 and a continuation-in-part of U.S. patent application Ser. No. 07/605,843, filed Oct. 29, 1990.

BACKGROUND OF THE INVENTION

1. Field of the Invention

The present invention relates to a fetal electrode product and a connector device for use in monitoring fetal heart rate. The device electrically connects fetal and maternal electrodes to a plate support on the body of an expectant mother.

2. Discussion of Related Art

U.S. patent applications Ser. Nos. 605,843 and 661,253 (to be referred to as "Ser. Nos. '843 and '253") are incorporated by reference. They disclose various plug connector and leg plate embodiments in which a male type plug connector is inserted into a female type socket connector within an opening in the leg plate for establishing electrical connection therebetween. The male type plug connector has contacts which face outwardly and the female type socket connector has contacts which face inwardly for engaging the outwardly facing contacts of the male type plug connector.

Some countries have A.C. wall outlets whose openings are of a size such that the male type plug connector may be inserted into them by mistake. This raises a safety issue because the male type plug connector is normally in electrical connection with fetal and maternal electrodes, which are within the mother. The male type plug connector has contacts which face outwardly so that wall outlet sockets could electrically connect with them if the connector is inserted.

The possibility of making electrical connection between an A.C. wall outlet and the mother constitutes a safety hazard which should be avoided. It would therefore be desirable to change the male type plug connector into some other type which is incapable of making such electrical connection when inserted into the wall outlet by mistake.

SUMMARY OF THE INVENTION

The present invention is directed to a fetal electrode product and a connector device for electrically connecting fetal and maternal electrodes to a plate support on the body of an expectant mother. The connector device includes means for electrically connecting fetal and maternal electrodes with a remote fetal monitoring device. Preferably, the fetal electrode product has a female connector is in electrical connection with the electrodes and the connector device has a male connector which is in electrical connection with a remote fetal monitoring device. The female connector engages the male connector to establish electrical connection therebetween.

BRIEF DESCRIPTION OF THE DRAWINGS

For a better understanding of the present invention, reference is made to the following description and accompanying drawings, while the scope of the invention is set forth in the appended claims.

FIG. 1 is a perspective view of the leg plate and female socket connector prior to engagement in accordance with a flat side embodiment of the present invention.

FIG. 2 is a perspective view of the female socket connector of FIG. 1.

FIG. 3 is an end view of FIG. 2.

FIG. 4 is an end view of the leg plate of FIG. 1.

FIG. 5 is a perspective view of the leg plate and female socket connector prior to their engagement in accordance with another flat side embodiment of the present application.

FIG. 6 is perspective view of the leg plate and female socket connector prior to their engagement in accordance with a ring contact embodiment of the present invention.

DESCRIPTION OF THE PREFERRED EMBODIMENT

FIG. 1 shows a fetal electrode product in accordance with the invention, as portion of which being the same as a conventional fetal electrode product (in accordance with U.S. Pat. No. 28,990) which includes a guide tube 4, driving tube 6 which is of a smaller diameter than that of the guide tube 4, and a twisted pair of wires 8 with one end each connected to respective fetal and maternal electrodes 10, 12. A nonconductive plastic holder 14 electrically insulates the fetal and maternal electrodes 10 and 12 from each other.

The fetal electrode 10 is in the form of a spiral electrode having a pointed end which is driven into contact with the fetal epidermis. The maternal electrode 12 is engaged by slots 16 at the forward end of the driving tube 6 to enable the pointed end of the fetal electrode 10 to rotate and be driven into the fetal epidermis by rotation of the driving tube 6.

A female socket connector 18, in accordance with the present invention, has an external diameter which is less than the inside diameter of the driving tube 6. Since the outer diameter of the guide tube 4 must be small enough to avoid harming the mother during its insertion, an outer diameter of about 0.315 inches is acceptable; the driving tube 6 and the plastic holder 14 must have even smaller external diameters to fit in the guide tube.

The female socket connector 18 has a hollow rod-shaped housing 20 in which a passage 22 extends inwardly of the housing from an open end 24. The passage 22 has a cross-section defined by two vertical sides and two convexly curved sides which extend between the vertical sides. Two contacts 26, 28 are recessed back from the open end 24 and face each other within the passage 22. One contact is in electrical connection with the fetal (spiral) electrode 10 and the other is in electrical connection with the maternal (spade) electrode 12 via respective wires of the twisted wire pair 8.

FIGS. 2 and 3 show that the housing 20 has two outwardly facing rod-shaped flats 30 each on a respective side of the housing 20. The housing 20 also has a pair of detents 32 which are recesses in the external surface of the housing.

FIG. 1 also shows a leg plate 34, which contains a printed circuit board (PCB) 36. The leg plate, shown in outline only, is identical to any of the leg plates which contain a printed circuit board as described in Ser. Nos. '843 and '253, except that, instead of barrel contacts, a male plug connector is employed. Similarly, the printed circuit board, the twisted wire pair with fetal and maternal electrodes are identical to that described in Ser. Nos. '843 and '253.

The leg plate 34 has a housing and a base secured to each other where the base has a ground electrode. One of the housing and the base makes provision, such as with a belt, for securing the same to the expectant mother's leg or abdominal region so that the ground electrode comes into electrical contact with her body. The leg plate may be considered a plate support on the mother's body.

The leg plate has a entrance opening 38 which communicates with an internal passage 40 within the housing 42 of the leg plate. The housing 42 defines the opening 38 by two oppositely facing flat walls 44 and two oppositely facing concavely curved walls 46. The internal periphery of the opening 38 matches the external shape of the housing 20 of the female connector 18 (compare FIGS. 3 and 4). This configuration guides the insertion of the female socket connector 18 into the opening 38 into a predetermined relative orientation to ensure the electrical connection is established with both contacts of a male plug connector 48.

The male plug connector 48 extends inside the passage 40 and has flat sides 50 in alignment with the flat walls 44 of the opening 48. The male plug connector 48 also has two convexly curved sides 52 which extend between the flat sides 50 and on which is a respective conductive contact 54. This conductive contact may be a metallic plate or coating. Two plug terminals 56 extend from an end of the male plug connector 48 and each is in electrical connection with a respective one of the conductive contacts 54.

A vertically extending bulkhead or body 58 is mounted (such as by soldering) on top of the PCB 36 and has two outlet terminals 60, into which may be inserted the two plug terminals 56 simultaneously for establishing electrical connection.

The PCB 36 has two input terminals as disclosed in U.S. patent Ser. No. 661,253. The two input terminals are connected to the two outlet terminals 60 via respective leads 62. Protrusions 64 extend inwardly within the passage 40 and are configured to engage with the detents 32 of the female connector 18 to releasably retain the female socket connector 18 to the male plug connector 48.

After plugging the male plug connector 48 into the outlet terminals 60 of the bulkhead 58, the male plug connector is ready to be inserted into the female socket connector 18. This requires that the female socket connector 18 be inserted into the passage 40 as far as possible. In order to ensure that electrical connection is effected between the contacts, the female socket connector 18 may be inserted through the opening 38 only when the flat sides 50 are in alignment against the flat walls 44 of the leg plate housing 42.

The female socket connector 18 is inserted onto the male plug connector 48, essentially shrouding the same. The male plug connector 48 has a forward end 66 which is tapered to facilitate insertion of the male plug connector into the opening 24 of the female socket connector 18. The contacts 26 resiliently bias in response to insertion of the male plug connector 48 within the passage 22 so as to maintain electrical connection between the contacts 26, 54. Thus, when inserting, the tapered forward end 66 eventually pushes the contacts 26 outward so that they exert a biasing force against the contact 54 thereafter.

The female socket connector 18 is inserted until the protrusions 64 and detents 32 engage each other, at which the connectors 18, 48 snap together by a holding force which tends to resist inadvertent separation, i.e., an intentional manual pulling force is required to effect separation. Further insertion of the female socket connector 18 relative to the male plug connector 48 beyond this protrusion/detent engagement is prevented by the bulkhead 58, which is in a path to block such further insertion. Also shown is a base 74 with ground electrode 76 and output means 78, which are the same as for any of the embodiments of Ser. Nos. '843 and '253. The base and housing are snapped together. The bulkhead 58 is interposed electrically between the male connector 48 and two leads of the output means 78. The ground electrode 76 is in electrical connection with another lead of the output means 78.

FIG. 5 shows another embodiment in which the male plug connector 48 protrudes through the opening 38 because the bulkhead 58 is positioned closer to the opening 38 than it was for the embodiment of FIG. 2. The protrusions 64 each lie on a respective one of the flat sides adjacent the opening 38 and the detents 32 are almost adjacent to the forward end of the female socket connector 18. When inserting the male plug connector 48 within the passage 22 of the female socket connector, the female socket connector 18 shrouds the male plug connector 48 until engagement between the protrusions and detents is effected. Instead of the bulkhead 58 effecting blocking, a portion of the leg plate housing 42 immediately adjacent the opening 38 may serve to block further insertion of the female socket connector onto the male plug connector.

Also, the male plug connector 48 may have leads soldered to terminals of the bulkhead 58 and be fastened to the bulkhead 58 by means of a screw 68 or other fastener. The bulkhead 58 may be soldered to the PCB 36 or be screwed into threaded holes (not shown) in the PCB 36. The leg plate, printed circuit board, female socket connector, twisted wire pair and electrodes are otherwise the same as that of FIG. 1.

FIG. 6 more closely resembles the embodiments of Ser. Nos. '843 and '253 by employing ring contacts 70 on the male plug connector and barrel contacts 72 within the passage 22 of the female socket connector 18. These connectors 18, 48 are otherwise identical to any of the other previously described embodiments. An advantage of the ring type contacts is that no particular orientation configuration is needed. Like the other embodiments, a detent/protrusion engagement may be employed to releasably lock the connectors together. The bulkhead 58 also blocks further relative insertion of the female socket connector onto the male plug connector beyond that which would result in disconnection of the electrical connection between the ring contacts and barrel contacts.

The male plug connector of FIG. 6 may project instead out of the leg plate housing in the same manner in which the male plug connector of FIG. 5 projects out of the leg plate housing, so as to provide for a further embodiment. The female socket connector engages the male plug connector in the same manner to effect electrical connection.

The connectors 18, 48 of any embodiment may have any shape. When one connector shrouds the other, some surfaces of the connectors face each other. Preferably, such surfaces complement each other in shape for effecting engagement to ensure maintenance of electrical contact therebetween. It does not make a difference which contact of any female socket connector electrically connects with which leg plate contact so long as both contacts of the female connector are in electrical connection.

The detents and protrusions of each embodiment may be exchanged with each other, i.e., the female socket connector may have the protrusions and the male plug connector of the leg plate may have the detents or vice versa. Instead of engaging with separate detents/protrusions, the contacts themselves may provide the same function by having at least one contact of one connector located in a recess in such connector and by having a corresponding contact of another connector bias into the recess after it reaches the recess during the insertion. Any other type of means for releasably retaining the male and female connectors together, such as by friction fitting, may be used instead of detents and protrusions.

Further, where any embodiment shows various components for accomplishing the same task accomplished by different components of another embodiment, the components are interchangeable between the embodiments. For instance, any embodiment could secure the male plug connector to the bulkhead either by plug in as in FIG. 1 or by screwing in and soldering the leads as in FIG. 5. The bulkhead of any embodiment may be secured to either the printed circuit board or to the leg plate housing.

If the female connector of any of the embodiments is inserted within a wall socket outlet by mistake, no electrical connection is effected thereby because the body of the female connector surrounds its contacts. In other words, there are no contacts on its outer periphery that would be accessible for making electrical connection within the wall outlet. Thus, a potential safety hazard is eliminated even though the female connector is electrically connected to fetal and maternal electrodes within the expectant mother. The body of the female connector is of a thickness and composition which effectively insulates the contacts from making electrical connection within the wall outlet through the body.

While the foregoing description and drawings represent the preferred embodiments of the present invention, it will be understood that various changes and modifications may be made without departing from the spirit and scope of the present invention.

What is claimed is:

1. A connector device for use in monitoring fetal heart rate, comprising:
    a housing;
    electrical connection means for making electrical connection between a remote fetal monitoring device and fetal and maternal electrodes, the connection means including a male plug connector and output means which are electrically connected together within the housing, the output means being adapted for making electrical connection with the remote fetal monitoring device, the electrical connection means also including a female socket connector engaging the male plug connector for establishing electrical connection therebetween, the female socket connector adapted to be electrically connected with the fetal and maternal electrodes;
    releasable retaining means for releasably retaining the connectors together when the electrical connection is established between the connectors;
    a base;
    ground electrode means supported by the base for providing an electrical ground;
    means for electrically connecting the ground electrode means with the output means and for securing the base to the housing; and
    means for securing one of the base and the housing to an expectant mother's leg so that the ground electrode means is in electrical contact with the mother and thereby provide the electrical ground.

2. A device as in claim 1, wherein the releasable retaining means includes an engaging protrusion and detent, the protrusion extending outwardly from one of the connectors and the detent extending inwardly from an adjacent external surface of the other of the connectors.

3. A device as in claim 1, wherein the housing has an internal passage terminating at an open entrance, the male plug connector extending within the passage.

4. A device as in claim 1, further comprising:
    a bulkhead body within the housing, the electrical connection means including socket terminals in the bulkhead body and also including plug terminals each extending from a common end of the male plug connector and into electrical contact with a respective one of the socket terminals, the socket terminals being in electrical contact with the output means, the plug terminals and the socket terminals being releasably engageable with each other.

5. A device as in claim 4, wherein the housing has an internal passage terminating at an open entrance, the male plug connector extending within the passage, the female socket connector shrouding the male plug connector within the passage, the bulkhead body being in a path of insertion of the female socket connector so that the female socket connector is blocked against being further inserted into the housing by the bulkhead body when the electrical connection between the connectors is established.

6. A device as in claim 1, wherein the male plug connector has an end which is tapered for facilitating insertion of the male plug connector within the female socket connector.

7. A device as in claim 1, wherein the connector have surfaces which cooperate for guiding insertion of the male plug connector into the female socket connector.

8. A device as in claim 7, wherein the housing has a passage into which is inserted the female socket connector, the passage having an entrance configured for guiding insertion of the female socket connector into the passage.

9. A device as in claim 1, wherein the electrical connection means includes a printed circuit board within the housing for electrically connecting the male plug connector and the output means together.

10. A connector device for use in monitoring fetal heart rate, comprising:
    a housing;
    electrical connection means for making electrical connection between a remote fetal monitoring device and fetal and maternal electrodes, the connection means including a male plug connector and output means which are electrically connected together within the housing, the output means being adapted for making electrical connection with the remote fetal monitoring device, the electrical connection means also including a female socket connector engaging the male plug connector for establishing electrical connection therebetween, the female socket connector adapted to be electrically connected with the fetal and maternal electrodes;

releasable retaining means for releasably retaining the connectors together when the electrical connection is established between the connectors;

a bulkhead body within the housing, the electrical connection means including socket terminals in the bulkhead body and also including plug terminals each extending from a common end of the male plug connector and into electrical contact with a respective one of the socket terminals, the socket terminals being in electrical contact with the output means, the plug terminals and the socket terminals being releasably engageable with each other, the connection means including a printed circuit board within the housing for electrically connecting the male connector and the output means together via the bulkhead body, the bulkhead body extending from the printed circuit board.

11. A connector device for use in monitoring fetal heart rate, comprising:

a housing;

electrical connection means for making electrical connection between a remote fetal monitoring device and fetal and maternal electrodes, the electrical connection means including a male plug connector and output means which are electrically connected together within the housing, the output means being adapted for making electrical connection with the remote fetal monitoring device;

a base with a ground electrode means supported by the base for providing an electrical ground;

means for electrically connecting the output means with the ground electrode means and for securing the base and the housing together; and means for securing one of the base and the housing to a leg of an expectant mother so that the ground electrode means is in electrical contact with the mother and thereby provide the electrical ground.

12. A device as in claim 11, wherein the male plug connector projects outwardly from the housing.

13. A device as in claim 11, wherein the housing has an internal passage which terminates at an open end, the male plug connector extending within the internal passage.

14. A device as in claim 11, wherein the male plug connector has an end which is tapered.

15. A fetal electrode product for use in monitoring fetal heart rate, comprising:

a fetal electrode and a maternal electrode secured to a holder made of an insulating material;

an elongated flexible driving tube for rotating said holder;

a female socket connector having an outer dimension less than an inner dimension of said driving tube so that said driving tube can be pulled over said female socket connector after said fetal electrode has been attached to a fetus, said female socket connector including an internal channel and at least two spaced apart electrical contacts within said channel, and an elongated pair of insulated wires each electrically connecting one of said electrodes to one of said contacts.

16. A product as in claim 15, wherein said contacts are spaced circumferentially from each other and secured to a surface of the female socket connector defining said channel.

17. A product as in claim 15, wherein said contacts are spaced axially from each other.

18. A product as in claim 15, wherein said connector is elongated with the contacts separated from each other in a direction of elongation of the connector.

19. A product as in claim 15, wherein said connector is elongated and has at least a portion whose cross-section is cylindrical, the contacts being annular.

20. A product as in claim 15, wherein said connector has a distal portion which is tapered, said wires extending within the distal portion, said connector having a proximal portion spaced from said distal portion, said internal channel being open at a proximal end of said proximal portion.

21. A product as in claim 15, wherein said connector and said contacts are elongated in a common direction, said contacts facing each other.

22. A product as in claim 21, said connector having two external sides which are flat and face away from each other.

23. A product as in claim 15, wherein said connector has an outward facing surface and a detent on said surface.

24. A product as in claim 15, wherein said connector has a detent located on a wall which defines the internal channel.

* * * * *